US006387654B1

(12) United States Patent
Liaw et al.

(10) Patent No.: US 6,387,654 B1
(45) Date of Patent: May 14, 2002

(54) BACTERIAL STRAINS AND FERMENTATION PROCESSES FOR THE PRODUCTION OF 2-KETO-L-GULONIC ACID

(75) Inventors: Hungming J. Liaw, Champaign; Robert L. Kowzic, Jr., Decatur; John M. Eddington, Decatur; Yuequin Yang, Decatur, all of IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 09/565,117

(22) Filed: May 4, 2000

(51) Int. Cl.[7] .......................... C12P 39/00; C12P 17/04; C12P 7/40
(52) U.S. Cl. .......................... 435/42; 435/126; 435/136
(58) Field of Search .......................... 435/42, 126, 136

(56) References Cited

U.S. PATENT DOCUMENTS

| | | | |
|---|---|---|---|
| 2,421,611 A | 6/1947 | Gray | 195/47 |
| 3,043,749 A | 7/1962 | Huang | 195/47 |
| 3,234,105 A | 2/1966 | Motizuki et al. | 195/49 |
| 3,907,639 A | 9/1975 | Makover et al. | 195/36 |
| 3,912,592 A | 10/1975 | Makover et al. | 195/31 |
| 3,998,697 A | 12/1976 | Sonoyama et al. | 195/47 |
| 4,866,178 A | 9/1989 | Venturello et al. | 544/406 |
| 4,877,735 A | 10/1989 | Nogami et al. | 435/138 |
| 4,892,823 A | 1/1990 | Imai et al. | 435/138 |
| 4,933,289 A | 6/1990 | Imai et al. | 435/253.3 |
| 4,935,359 A | 6/1990 | Yin et al. | 435/138 |
| 4,945,048 A | 7/1990 | Uchihori et al. | 435/105 |
| 4,960,695 A | 10/1990 | Hoshino et al. | 435/42 |
| 5,082,785 A | 1/1992 | Manning et al. | 435/252.32 |
| 5,312,741 A | 5/1994 | Hoshino et al. | 435/42 |
| 5,437,989 A | 8/1995 | Asakura et al. | 435/190 |
| 5,474,924 A | 12/1995 | Nogami et al. | 435/138 |
| 5,541,108 A | 7/1996 | Fujiwara et al. | 435/252.1 |
| 5,705,373 A | 1/1998 | Yamaguchi et al. | 435/138 |
| 5,747,306 A | 5/1998 | Oka et al. | 435/138 |
| 5,834,231 A | 11/1998 | Stoddard et al. | 435/42 |
| 5,989,891 A | 11/1999 | Liaw et al. | 435/244 |

FOREIGN PATENT DOCUMENTS

| | | |
|---|---|---|
| CN | 1081470 | 2/1994 |
| EP | 0 213 591 | 3/1987 |
| EP | 0 221 707 | 5/1987 |
| EP | 0 278 447 | 8/1988 |
| EP | 0 518 136 | 12/1992 |
| EP | 0 832 974 | 4/1998 |
| JP | 41-159 | 1/1966 |
| JP | 41-160 | 1/1966 |
| JP | 41-5907 | 3/1966 |
| JP | 7-67673 | 3/1995 |
| JP | 7-250671 | 10/1995 |
| SU | 526660 | 10/1976 |
| WO | WO 98 33885 | 8/1998 |

OTHER PUBLICATIONS

Wang et al., "Purification and characterization of a *Bacillus cereus* exochitinase", Enzyme Microb. Technol. 28 (6) : 492–498 (2001).*

Johnson et al., "Biocerin: an antibiotic produce by *Bacillus cereus*", J. Bact. 57 : 63–65 (1949).*

Follettie, M.T., "DNA Technology for *Corynebacterium glutamicum*: Isolation and Characterization of Amino Acid Biosynthetic Genes," Ph.D. Thesis, Massachusetts Institute of Technology (1989).

*Biotechnology*—A Comprehensive Treatise in 8 Volumes, Kieslich, K., ed., Verlag Chemie, Weinheim, Germany, vol. 6a, pp. 436–437 (1984).

Martin, C.K.A., and Perlman, D., "Conversion of L–Sorbose to 2–Keto–L–gulonic Acid by Mixtures of Immobilized Cells of *Gluconobacter melanogenus* IFO 3293 and Pseudomonas Species," *Eur. J. Appl. Microbiol.* 3:91–95 (1976).

English Translation of JP 41–159 (Document AL1).

English Translation of JP 41–160 (Document AM1).

English Translation of JP 41–5907 (Document AN1).

Tsukada, Y., and Perlman D., "The Fermentation of L–Sorbose by *Gluconobacter melanogenus*: General Characteristics of the Fermentation," *Biotechnology and Bioengineering XIV*:799–810 (1972).

"The Genetic Improvement of Product Formation," in Molecular Biology and Biotechnology, Walker, J.M., and Gingold, E.B., eds., Royal Society of Chemistry, London, Great Britain, pp. 15–20 (1988).

Yin, G.–l., et al., "Studies on the Production of Vitamin C Precursor 2–Keto–L–Gulonic Acid from L–Sorbose by Fermentation. I. Isolation, Screening and Identification of 2–Keto–L–Gulonic Acid Producing Bacteria," *Acta Microbiol. Sinica* 20:246–251 (1980).

Yin, G.–l., et al., "Studies on the Production of Vitamin C Precursor 2–Keto–L–Gulonic Acid from L–Sorbose by Fermentation," *Acta Microbiol. Sinica* 21:185–191 (1981).

(List continued on next page.)

*Primary Examiner*—Sandra E. Saucier
(74) *Attorney, Agent, or Firm*—Sterne, Kessler, Goldstein & Fox P.L.L.C.

(57) ABSTRACT

The present invention relates to novel bacterial strains belonging to the genera Gluconobacter, Ketogulonogenium and Bacillus useful for the production of 2-keto-L-gulonic acid. The present invention further relates to the use of these strains for the production of 2-keto-L-gulonic acid in mixed culture by fermentative conversion of D-sorbitol. The present invention further relates to the strains of the present invention transformed by a vector.

36 Claims, 4 Drawing Sheets

OTHER PUBLICATIONS

English Translation of Yin, G.–L., et al., "Studies on the Production of Vitamin C Precursor 2–Keto–L–Gulonic Acid from L–Sorbose by Fermentation. I. Isolation, Screening and Identification of 2–Keto–L–Gulonic Acid Producing Bacteria," *Acta Microbiol. Sinica* 20:246–251 (1980).

English Translation of Yin, G.–l., et al., "Studies on the Production of Vitamin C Precursor 2–Keto–L–Gulonic Acid from L–Sorbose by Fermentation," *Acta Microbiol. Sinica* 21:185–191 (1981).

English language abstract of SU 526660 (Document A01), Derwent World Patents Index, WPI Accession No.: 77–48308Y/27.

English language abstract of CN 1081470 (Document A02), Derwent World Patents Index, WPI Accession No.: 95–155907/21.

English language abstract of JP 7–250671 (Document A13), Japio No. 04958071.

* cited by examiner

*G. oxydans* ADM 205-95
1.5 mL Vial of frozen culture

Shaker Flask
30°C, 240 rpm
16-24 hours

*K. robustus* ADM 178-49
1.5 mL Vial of frozen culture

Propagation Fermentor
30°C, 1.8-2.0 VVM, 1-3 psi
500 rpm, 16-24 hours

Shaker Flask
30°C, 240 rpm
16-24 hours

Seed Fermentor
30°C, 1.8-2.0 VVM, 1-3 psi
500 rpm, 16-24 hours

*B. cereus* ADM C12B
30°C, 240 rpm
1.5 mL Vial of frozen culture

Propagation Fermentor
30°C, 1.8-2.0 VVM, 1-3 psi
500 rpm, pH 6.7, 16-24 hours

Shaker Flask
30°C, 240 rpm
16-24 hours

Main Fermentor
(L-sorbose producing stage)
30°C, 1.8-2.0 VVM, 1-3 psi
650 rpm, 12-16 hours
no pH control

Seed Fermentor
30°C, 1.8-2.0 VVM, 1-3 psi
500 rpm, pH 6.7, 16-24 hours

Propagation Fermentor
30°C, 1.8-2.0 VVM, 1-3 psi
500 rpm, 12-24 hours pH adjusted to 6.7

Main Fermentor
(2-KLG producing stage)
30°C, 1.8-2.0 VVM, 1-3 psi
650 rpm, pH 6.7
38-45 hours

Figure 1

ADM 205-95 (NRRL B-30266)

ATCC 621

ADM X6L (NRRL B-21627)

ADM 86-96 (NRRL B-21630)

ADM 178-49 (NRRL B-30265)

ADM-1A9 (NRRL B-30268)

ADM-C12B (NRRL B-30267)

BACTERIAL STRAINS AND FERMENTATION PROCESSES FOR THE PRODUCTION OF 2-KETO-L-GULONIC ACID

BACKGROUND OF THE INVENTION

1. Field of the Invention

The present invention relates to the fields of microbiology and fermentation technology. The present invention further relates to the use of novel bacterial strains, ingredients and processes useful for the fermentative production of 2-keto-L-gulonic acid from D-sorbitol.

2. Related Art

2-Keto-L-gulonic acid ("2-KLG") is a significant intermediate in the preparation of L-ascorbic acid (vitamin C), an essential nutrient. 2-KLG has been synthesized in the past on an industrial scale using the Reichstein method (*Helvetica Chimica Acta* 17:311 (1934)). This method, however, has a number of disadvantages for commercial application, including the use of large quantities of solvents and the involvement of a number of complex reaction steps.

Accordingly, as an alternative to the Reichstein method, a number of processes employing one or more microorganisms have been developed to produce 2-KLG by fermentation. U.S. Pat. No. 2,421,611, for example, discloses a method involving microbial oxidation of D-glucose to 5-keto-D-gluconic acid, followed by chemical or microbial reduction to L-idonic acid and subsequent microbial oxidation to 2-KLG. U.S. Pat. No. 3,998,697 discloses a similar process involving the microbial oxidation of D-glucose to 2,5-diketo-D-gluconic acid, followed by microbial reduction to 2-KLG.

These methods, however, also suffer from a number of disadvantages that reduce their usefulness in commercial production of 2-KLG. For example, the chemical reduction steps in these methods (i.e. the reduction of 5-keto-D-gluconic acid to L-idonic acid and 2,5-diketo-D-gluconic acid to 2-KLG) are accompanied by problems with controlling the stereochemistry of reduction (thus producing D-gluconic acid and 2-keto-D-gluconic acid, respectively, as byproducts) which, in turn, reduces the yield of 2-KLG. Alternatively, when this reduction is performed by one or more microorganisms, excess sugar is required to provide an energy source for the reduction, which also reduces the yield of 2-KLG.

In view of these problems, alternate pathways have been employed for the fermentative production of 2-KLG. A number of processes have been developed which involve oxidation of L-sorbose to 2-KLG via a sorbosone intermediate that employ a wide range of microorganisms from the genera Gluconobacter, such as *Gluconobacter oxydans* (U.S. Pat. Nos. 4,935,359; 4,960,695; 5,312,741; and 5,541,108), Pseudogluconobacter, such as *Pseudogluconobacter saccharoketogenes* (U.S. Pat. No. 4,877,735; European Patent No. 221 707), Pseudomonas, such as *Pseudomonas sorbosoxidans* (U.S. Pat. Nos. 4,933,289 and 4,892,823), and mixtures of microorganisms from these and other genera, such as Acetobacter, Bacillus, Serratia, Mycobacterium, and Streptomyces (U.S. Pat. Nos. 3,912,592; 3,907,639; and 3,234,105).

These processes, however, suffer from certain disadvantages that limit their usefulness for commercial production of 2-KLG. For example, the processes referenced above that employ *G. oxydans* also require the presence of an additional "helper" microbial strain, such as *Bacillus megaterium*, or commercially unattractive quantities of yeast or growth components derived from yeast in order to produce sufficiently high levels of 2-KLG for commercial use. Similarly, the processes that employ Pseudogluconobacter can require medium supplemented with expensive and unusual rare earth salts or the presence of a helper strain, such as *B. megaterium*, and/or the presence of yeast in order to achieve commercially suitable 2-KLG concentrations and efficient use of sorbose substrate. Other processes that employ *Pseudomonas sorbosoxidans* also include commercially unattractive quantities of yeast or yeast extract in the medium.

Other processes for the fermentative production of 2-KLG involving D-sorbitol as the starting material have also been developed. For example, 2-KLG can be produced from D-sorbitol with the aid of microorganisms of the genera Acetobacter, Bacterium or Pseudomonas which are capable of oxidizing D-sorbitol under aerobic conditions producing 2-KLG. However, according to this process, the yield of 2-KLG is low.

D-sorbitol as a starting material would be preferable to L-sorbose because it is less expensive. However, L-sorbose is more efficiently converted to 2-KLG. Therefore, a process that uses D-sorbitol as a starting material but provides L-sorbose for conversion combines the availability of D-sorbitol with the higher yield provided by L-sorbose. If part of the process is the conversion of D-sorbitol to L-sorbose, which is then converted to 2-KLG, then efficient production can be attained.

The conventional processes to produce 2-KLG from D-sorbitol via L-sorbose have been developed through two stage fermentation in which D-sorbitol is first converted to L-sorbose by one organism, and then L-sorbose is fed to another organism or mixed culture in a different medium to produce 2-KLG in a separate fermentor. A single stage fermentation using a single medium for a mixed culture to produce 2-KLG directly from D-sorbitol via L-sorbose in the same fermentor would provide a simpler and shorter fermentation with lower cost and higher yield for the production of 2-KLG from D-sorbitol versus the conventional method using two stage fermentation.

Accordingly, there still remains a need in the art for more efficient and economical 2-KLG-producing microorganism strains and processes.

SUMMARY OF THE INVENTION

The present invention provides microorganism strains and processes which efficiently produce 2-KLG from D-sorbitol via L-sorbose in a mixed culture. The invention provides a simpler and shorter fermentation with lower cost and higher yield for the production of 2-KLG from D-sorbitol versus the conventional method using two stage fermentation.

A further embodiment of the present invention is directed to strains for the production of 2-KLG in cooperation with helper strains.

Another embodiment of the present invention provides a process for the production of 2-KLG in which the fermentation medium contains soybean products.

An additional embodiment of the present invention is to provide the bacterial strains of the present invention transformed by a vector, and a method for the transformation of the bacterial strains by a vector.

These and other embodiments are accomplished by the present invention, which, in a first embodiment, is directed to a culture of a microorganism strain having the identifying characteristics of any of the microorganism strains NRRL B-30266, NRRL B-30265, NRRL B-30267 or NRRL B-30268, or mutants thereof derived from the strains.

Other features and advantages of the present invention will be set forth in the detailed description of preferred embodiments that follows, and in part will be apparent from the description or can be learned by practice of the invention. These features and advantages of the invention will be realized and attained by the methods particularly pointed out in the written description and claims hereof.

It is to be understood that both the foregoing general description and the following detailed description are exemplary and explanatory only and are intended to provide further explanation of the invention as claimed.

BRIEF DESCRIPTION OF THE FIGURES

FIG. 1 is a depiction of the single stage fermentation modified to employ three organisms and soluble soy isolates ADM Soy Soluble and ADM RO Concentrate. The three organisms, G. oxydans NRRL B-30266 (ADM 205-95), K. robustum NRRL B-30265 (ADM 178-49) and B. cereus NRRL B-30267 (ADM C12B), were cultivated separately through propagation/seed stage before they were inoculated to the main fermentation medium.

DETAILED DESCRIPTION OF THE PREFERRED EMBODIMENTS

In a first embodiment, the present invention is directed to a biologically pure culture of a microorganism strain comprising the identifying characteristics of a strain selected from the group consisting of NRRL B-30266, NRRL B-30265, NRRL B-30267 and NRRL B-30268, or a mutant thereof derived from the strain. The microorganism strains of the present embodiment are capable of producing 2-KLG from D-sorbitol by fermentation in mixed culture. In addition to the biologically pure strains, functional equivalents, subcultures, mutants and variants thereof can also be employed for the production of 2-KLG. Preferably, the mixed culture comprises at least two different microorganism strains which are capable of producing at least about 40 g/L of 2-KLG from D-sorbitol, more preferably at least about 60 g/L, and most preferably at least about 80 g/L.

In another embodiment, the present invention is directed to a process for the production of 2-KLG utilizing the inventive microorganism strains. The process (which as used herein, is synonymous with method) comprises culturing a microorganism strain comprising the identifying characteristics of NRRL B-30265 or a mutant thereof in mixed culture with a microorganism strain capable of converting D-sorbitol to L-sorbose, in a medium containing D-sorbitol, for a time sufficient for said D-sorbitol to be converted to 2-KLG and recovering the 2-KLG. The inventive fermentation process comprises cultivating the microorganisms in a synthetic or natural culture medium for a sufficient time and then isolating the accumulated 2-KLG from the culture medium and/or cells of the microorganisms.

According to the inventive fermentation process, the mixed culture comprises at least one microorganism strain that is capable of producing L-sorbose from D-sorbitol. Any microorganism or mixture of microorganisms that can convert D-sorbitol to L-sorbose in the presence of the 2-KLG producing strain(s) or a mutant or variant thereof while not adversely affecting its ability to convert L-sorbose to 2-KLG can be employed. Preferably, the microorganism employed is a strain of *Gluconobacter oxydans,* more preferably *G. oxydans* strain ATCC 621 or *G. oxydans* strain IFO 3293 or mutants thereof.

In a preferred embodiment, the mutant is selected from media containing more than 100 g/L or preferably more than 150 g/L of L-sorbose. More preferably, the L-sorbose producing microorganism is strain NRRL B-30266 (ADM strain 205-95), a mutant derived from *G. oxydans* strain ATCC 621.

Strain ADM 205-95 was deposited at the Agricultural Research Service Culture Collection (NRRL), 1815 North University Street, Peoria, Ill. 61604, U.S.A., on Feb. 25, 2000 under the provisions of the Budapest Treaty and assigned accession number NRRL B-30266.

Figure 2:
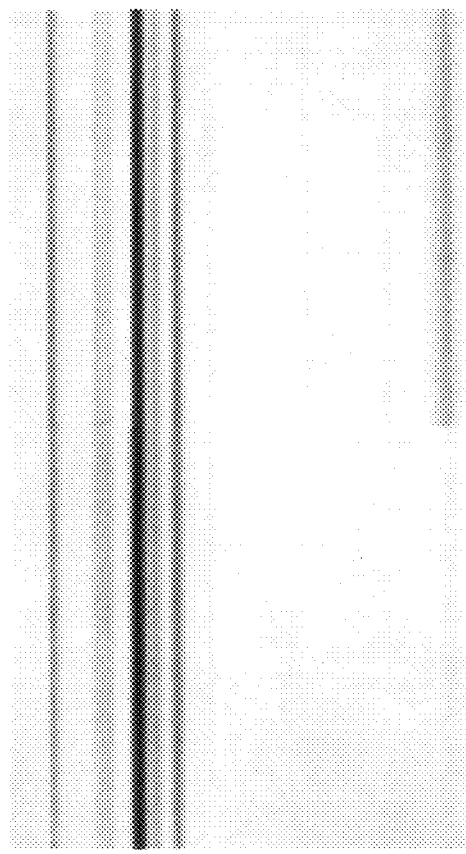
FIG. 2 is a depiction of the RiboPrint® patterns of bacterial strains capable of producing L-sorbose from D-sorbitol. RiboPrint® patterns were obtained from G. oxydans strain NRRL B-30266 (ADM 205-95) and G. oxydans strain ATCC 621.

RiboPrint® analysis involves hybridization of radiolabeled anti-sense RNA to the genetic material being studied, followed by detection of the labeled double-stranded hybrid using gel electrophoresis. RiboPrint® is an automated ribotyping system that generates and analyzes genetic fingerprints of bacteria. The genetic fingerprinting patterns are normalized digital representations of the genetic data for each sample. The patterns obtained by this method are useful for differentiating not only between organisms of different species, but also between different strains of the same species. RiboPrint® patterns obtained for strain NRRL B-30266 (ADM strain 205-95) and a comparative strain known to be capable of producing L-sorbose from D-sorbitol are depicted in FIG. 2.

In addition to biologically pure strain NRRL B-30266 (ADM 205-95), mutants and variants thereof can also be employed in the inventive process, provided that these mutants and variants are also capable of converting D-sorbitol to L-sorbose in the presence of the 2-KLG producing strain(s) or a mutant or variant thereof while not adversely affecting its ability to convert L-sorbose to 2-KLG.

As used herein, a "biologically pure" strain is intended to mean the strain separated from materials with which it is normally associated in nature. Note that a strain associated with other strains, or with compounds or materials that it is not normally found with in nature, is still defined as "biologically pure." A monoculture of a particular strain is, of course, "biologically pure."

According to this preferred embodiment of the present invention, the D-sorbitol starting material can be present in the medium prior to introduction of one or more of the microorganisms or can be added to the medium after introduction of one or more of the microorganisms, either all at once at the beginning or continuously or in installments over the course of cultivation.

In accordance with the inventive fermentation process, the mixed culture further comprises at least one microorganism strain that is capable of producing 2-KLG from L-sorbose.

Strain ADM 178-49 was deposited at the Agricultural Research Service Culture Collection (NRRL), 1815 North University Street, Peoria, Ill. 61604, U.S.A., on Feb. 25, 2000 under the provisions of the Budapest Treaty and assigned accession number NRRL B-30265. The characteristics of strain NRRL B-30265 (ADM 178-49) include, but are not limited to:

(1) Cell Morphology—gram-negative; can be gram variable in older cultures; pleiomorphic; short rods or coccobacilli; cells appear singly and in pairs; can form short chains or filaments; does not form spores;

(2) Colony Morphology—punctiform, convex, entire, smooth, butyrous and translucent; beige or light brown coloration in older colonies on some media;

(3) Motility: no motility observed in wet mounts prepared from liquid cultures or 2% agar plate cultures; motility observed by stabbing fresh culture into a plate of BUGM™ medium (available from Biolog, Inc., Cat. # 70001) that has been partially solidified using 0.3% to 0.4% agar; cells manufacture flagella under conditions used to observe motility;

(4) Temperature range: no growth observed at 4° C., 37° C. or 41° C., while good growth observed at 25° C., and 30° C.;

(5) pH range: no growth observed at pH 4.5; growth observed at pH 6.2; good growth observed at pH 7.2;

(6) Physiological characteristics:
   (a) catalase: positive;
   (b) oxidase: positive
   (c) gelatinase: negative;
   (d) aerobic, no growth under anaerobic conditions;
   (e) brown pigment formed from fructose;
   (f) acid is produced from ethanol;
   (g) dihydroxyacetone is not produced from glycerol;
   (h) does not form pellicle or ring within 24 hours in standing glucose or mannitol broth culture at pH in range of 4.0–5.0; and
   (i) sensitive to streptomycin; and (7) Cultural Characteristics:
   (a) growth in 3% NaCl: positive;
   (b) peptone-yeast extract-mannitol agar: growth;
   (c) Marine agar: slow growth;
   (d) BUGM™ and BUGM-G™: growth; and
   (e) Brain Heart Infusion agar: growth.

Figure 3:
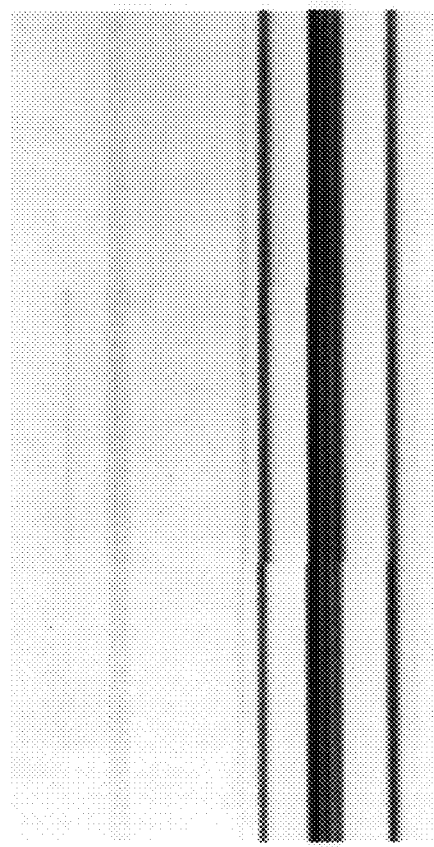
FIG. 3 is a depiction of the RiboPrint® patterns of bacterial strains capable of producing 2-KLG from L-sorbose. RiboPrint® patterns were obtained from the following bacterial strains: NRRL B-21627 (ADM X6L); NRRL B-21630 (ADM 86-96); and NRRL B-30265 (ADM 178-49).

(8) RiboPrint® Analysis:
RiboPrint® patterns obtained for strain NRRL B-30265 (ADM 178-49) and a number of comparative strains known to be capable of producing 2-KLG from L-sorbose are depicted in FIG. 3.

In addition to biologically pure strain NRRL B-30265 (ADM 178-49), mutants and variants thereof can also be employed in the inventive process, provided that these mutants and variants are also capable of producing at least about 40 g/L of 2-KLG from D-sorbitol in mixed culture.

As used herein, a mutant of a given strain of the present invention is derived from one of the strains of the present invention, namely, NRRL B-30266 (ADM 205-95), NRRL B-30265 (ADM 178-49), NRRL B-30267 (ADM C12B) or microorganism strain NRRL B-30268 (ADM 1A9). A mutant may or may not have the same identifying biological characteristics of the parent or progenitor strain, as long as the mutant aids in the fermentative production of 2-KLG.

Illustrative examples of suitable methods for preparing mutants and variants of the inventive microorganism strains include, but are not limited to: mutagenesis by irradiation with ultraviolet light or X-rays, or by treatment with a chemical mutagen such as nitrosoguanidine (N-methyl-N'-nitro-N-nitrosoguanidine), methylmethanesulfonate, nitrogen mustard and the like; gene integration techniques, such as those mediated by insertional elements or transposons or by homologous recombination of transforming linear or circular DNA molecules; and transduction mediated by bacteriophages such as P1. These methods are well known in the art and are described, for example, in J. H. Miller, *Experiments in Molecular Genetics,* Cold Spring Harbor Laboratory Press, Cold Spring Harbor, N.Y. (1972); J. H. Miller, *A Short Course in Bacterial Genetics,* Cold Spring Harbor Laboratory Press, Cold Spring Harbor, N.Y. (1992); M. Singer and P. Berg, *Genes & Genomes,* University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla. (1995); *Methods in Plant Molecular Biology and Biotechnology,* B. R. Glick and J. E. Thompson, eds., CRC Press, Boca Raton, Fla. (1993); and P. F. Smith-Keary, *Molecular Genetics of Escherichia coli,* The Guilford Press, New York, N.Y. (1989).

Mutated strains derived from the inventive microorganism strains using known methods are then preferably selected or screened for improved 2-KLG production potential or for other desirable properties related to their utility in producing 2-KLG from D-sorbitol. In a particularly preferred embodiment of the mutagenesis and screening approach to strain improvement, mutagenized cells are selected on the basis of their resistance to growth-inhibitory concentrations of partially derivatized or degraded 2-KLG, such as 2-KLG derivatives generated by autoclaving or other exposure to heat. In an alternative embodiment, the selective agent can be generated by other means of chemical modification of 2-KLG, including, but not limited to: amino-substitution to create 2-amino-L-gulonic acid or 2-amino-L-idonic acid; oxidation at the $C_6$ position to create 5-keto-glucaric acid; modifications leading to various thiol- or deoxy-derivatives or various unsaturated derivatives of 2-KLG; or by any other means that will be clear to individuals versed in the art.

In general, any period of time sufficient to produce 2-KLG in the culture medium can be used, and the instant process can be conducted by means of a variety of methods. Both microorganisms can be simultaneously inoculated in the medium at the initiation of cultivation. The L-sorbose-producing strain can be inoculated first and 2-KLG-producing strain subsequently inoculated after a period of cultivation. Both microorganisms can be inoculated separately into respective media, and then one is added to the other or vice versa either portionwise or continuously after a period of cultivation, followed by another period of cultivation. Preferably, the ratio of the amount of the 2-KLG-producing strain relative to the amount of the L-sorbose-producing strain is in the range of from about 10:1 to about 1:10, more preferably from about 5:1 to about 1:5.

For the process of the present invention, any suitable culturing method can be employed for the microorganisms used. The method of mixing can be determined in compliance with the properties of the specific microorganism to be employed. The incubation times, inoculation schedules and ratios of the microorganisms can be optimized for the specific microorganism employed. Namely, the ratio of the amount of the L-sorbose-producing microorganism to the 2-KLG-producing microorganism and the times of inoculations are preferably selected and determined in view of the growth rate of the respective microorganisms, the L-sorbose producing ability and the ability for converting L-sorbose into 2-KLG of the microorganisms involved, and in view of the properties of the media to be used.

In some cases, products obtained by treating the cells can also be used as a substitute for either one of the growing cells. Any products resulting from treating the cells of the inventive microorganisms, for instance, resting cells, lyophilized cells or immobilized cells, can be employed.

In the preferred embodiment of the present invention, the L-sorbose and 2-KLG-producing microorganisms can be inoculated with and cultivated in a medium which includes D-sorbitol. Preferably, the microorganism strains are cultivated in a natural or synthetic medium containing D-sorbitol for a sufficient period of time for 2-KLG to be produced, and the accumulated 2-KLG is subsequently isolated. Alternatively, a preparation derived from the cells of the microorganism strains can be contacted with D-sorbitol for a sufficient time and the accumulated 2-KLG can then be isolated.

As used herein, "a preparation derived from the cells" is intended to mean any and all extracts of cells from the culture broths of the inventive strain or a mutant or variant thereof, acetone dried cells, immobilized cells on or within supports, such as polyacrylamide gel, K-carrageenan, calcium alginate and the like, and similar preparations.

Any technique and/or method for the cultivation of microorganisms can be adopted. Cultivation of the inventive microorganism strain can be accomplished using any of the submerged fermentation techniques known to those skilled in the art, such as airlift, traditional sparged-agitated designs, or in shaking culture. The use of aerated and agitated submerged fermentors is particularly preferred.

The medium used herein can be solid or liquid, synthetic (i.e. man-made) or natural, and contains sufficient nutrients for the cultivation of the inventive microorganism strains. Preferably, the medium employed is a liquid medium, more preferably a synthetic liquid medium.

In the various embodiments of the process of the present invention, the starting material, D-sorbitol, can be present in the medium prior to introduction of the inventive microorganism strains or can be added to the medium after introduction of the strains, either all at once at the beginning or continuously or in installments over the course of cultivation, or can be generated in situ by fermentative conversion. The amount of D-sorbitol employed can be determined empirically by one skilled in the art, but is at least sufficient for the microorganism strains to produce at least about 40 g/L of 2-KLG. In this instant process, a concentration of D-sorbitol of about 20 to about 250 g/L in total is generally used and, in particular, a concentration of about 50 to about 200 g/L in total.

In addition to D-sorbitol, the natural or synthetic culture medium also contains a nitrogen source, suitable inorganic salts, and, as appropriate, various trace nutrients, growth factors and the like suitable for cultivation of the microorganism strain, and can also contain at least one supplementary carbon source. The amount of each of these additional ingredients to be employed is preferably selected to maximize 2-KLG production. Such amounts can be determined empirically by one skilled in the art according to the various methods and techniques known in the art. In addition, these additional ingredients can be added to the medium before the start of culturing, step-by-step or continuously during culturing.

In a particularly preferred embodiment of the present invention, the culture medium contains soybean products to supplement nutrients for the mixed cultures. Preferably, the soybean products are from the processing of soybeans to produce soy oil, soy proteins and other products.

In the process to separate oil, protein and carbohydrates from soybean, two parts of soluble components are separated after hexane extraction: alcohol washed soluble isolates and water washed soluble isolates. The alcohol washed soluble isolates are products from the stream of alcohol washed concentration of defatted soy flakes. For example, ADM Soy Soluble containing about 5–15% dry solid is the first product from this process. It contains about 4–10% protein, about 8–16% fat, about 30–60% sucrose, about 15–25% stachyose, about 3–9% raffinose and about 5–12% ash.

The water washed soluble isolates are products from the water processing of soy protein isolate using defatted soy flakes. ADM RO Concentrate containing about 2–6% dry solid is a product from this process. It contains about 13–21% protein, about 2–6% fat, about 18–28% sucrose, about 6–13% stachyose, about 1–5% raffinose, about 13–21% pentose and about 20–35% ash.

Preferably, the soybean products in the media comprise soy flour, soy protein and its hydrolysate, soy peptone, soy isolates, soluble soy isolates, soy whey or soy molasses. More preferably, the soybean products comprise soluble soy isolates or soy whey.

Illustrative examples of suitable supplemental carbon sources include, but are not limited to: other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol, inositol, mannitol and sorbitol.

Illustrative examples of suitable nitrogen sources include, but are not limited to: ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

Illustrative examples of suitable inorganic salts include, but are not limited to: salts of potassium, calcium, sodium, magnesium, manganese, iron, cobalt, zinc, copper and other trace elements, and phosphoric acid.

Illustrative examples of appropriate trace nutrients, growth factors, and the like include, but are not limited to: coenzyme A, pantothenic acid, pyridoxine-HCl, biotin, thiamine, riboflavin, flavine mononucleotide, flavine adenine dinucleotide, DL-6,8-thioctic acid, folic acid, Vitamin $B_{12}$, other vitamins, amino acids such as cysteine and hydroxyproline, bases such as adenine, uracil, guanine, thymine and cytosine, sodium thiosulfate, p- or r-aminobenzoic acid, niacinamide, nitriloacetate, and the like, either as pure or partially purified chemical compounds or as present in natural materials.

In a particularly preferred embodiment of the present invention, the main fermentation medium used for 2-KLG production contains about 100 g/L to about 200 g/L of D-sorbitol, from about 2 g/L to about 10 g/L dry solid of ADM Soy Soluble or ADM RO Concentrate, from about 10 g/L to about 30 g/L dry solid of corn steep liquor, and from about 0.2 m/L to about 0.4 ml/L antifoam, with pH from about 6.0 to about 7.0.

The culture conditions employed, including temperature, pH, aeration rate, agitation rate, culture duration, and the like, can be determined empirically by one of skill in the art to maximize 2-KLG production. The selection of specific culture conditions depends upon factors such as the particular inventive microorganism strain employed, medium composition and type, culture technique, and similar considerations.

In a particularly preferred embodiment of the present invention, cultivation takes place at a temperature in the range of 0° C. to 40° C., preferably 5° C. to 36° C., and even more preferably 20° C. to 34° C. and at a pH in the range of 5.0 to 9.0, preferably in the range of 5.5 to 8.5, more preferably about 6.0 to 8.0. The culture conditions employed can, of course, be varied by known methods at different timepoints during cultivation, as appropriate, to maximize 2-KLG production. In the present embodiment, 2-KLG is accumulated in the cells and/or culture medium.

In order to maintain the pH value of the medium as that most suitable for the enzymatic activity, any suitable acidic or basic agent can be added to the medium in a suitable amount at a suitable time during the cultivation. The same object can alternatively be accomplished by incorporating a suitable buffer or buffering agent into the medium at the beginning of the cultivation. For example, pH can be controlled using $NH_4OH$, $Ca(OH)_2$ or $CaCO_3$.

After cultivation for a sufficient period of time, such as, for example, from about 10 to about 150 hours, preferably from about 10 to about 80 hours, the 2-KLG that has accumulated in the cells and/or culture broth is isolated according to any of the known methods including ion exchange chromatography, gel filtration, solvent extraction, affinity chromatography, or any combination thereof Any method that is suitable with the conditions employed for cultivation can be used; illustrative examples of suitable methods for recovering 2-KLG are described in U.S. Pat. Nos. 5,474,924; 5,312,741; 4,960,695; 4,935,359; 4,877,735; 4,933,289; 4,892,823; 3,043,749; 3,912,592; 3,907,639 and 3,234,105.

According to one such method, the microorganisms are first removed from the culture broth by known methods, such as centrifugation or filtration, and the resulting solution concentrated in vacuo. Crystalline 2-KLG is then recovered by filtration and, if desired, purified by recrystallization. Similarly, 2-KLG can be recovered using such known methods as the use of ion-exchange resins, solvent extraction, precipitation, salting out and the like.

When 2-KLG is recovered as a free acid, it can be converted to a salt, as desired, with sodium, potassium, calcium, ammonium or similar cations using conventional methods. Alternatively, when 2-KLG is recovered as a salt, it can be converted to its free form or to a different salt using conventional methods.

The 2-KLG or its salt thus obtained can be used directly for conversion to L-ascorbic acid by esterification, followed by enolization and lactonization. Further, the 2-KLG can be converted to any conventional salt of ascorbic acid.

In an alternative embodiment of the present invention, the mixed culture comprises an additional microorganism strain which is capable of providing helper function. As used herein, "helper strain" is intended to mean a strain of a microorganism that increases the amount of 2-KLG produced in the inventive process. Suitable helper strains can be determined empirically by one skilled in the art. Illustrative examples of suitable helper strains include, but are not limited to, members of the following genera: Aureobacterium (preferably *A. liquefaciens* or *A. saperdae*), Corynebacterium (preferably *C. ammoniagenes* or *C. glutamicum*), Bacillus, Brevibacterium (preferably *B. linens* or *B. flavum*), Pseudomonas, Proteus, Enterobacter, Citrobacter, Erwinia, Xanthomonas and Flavobacterium.

Preferably, the helper microorganism strain is *Bacillus cereus*, more preferably the spore-forming *B. cereus* strain NRRL B-30267 (ADM C12B) or its mutant thereof. In a preferred embodiment, mutants of *B. cereus* strain NRRL B-30267 (ADM C12B) are selected to be incapable of producing spores. More preferably, the non-spore forming mutant strain NRRL B-30268 (ADM 1A9) is used in the inventive process.

Figure 4:
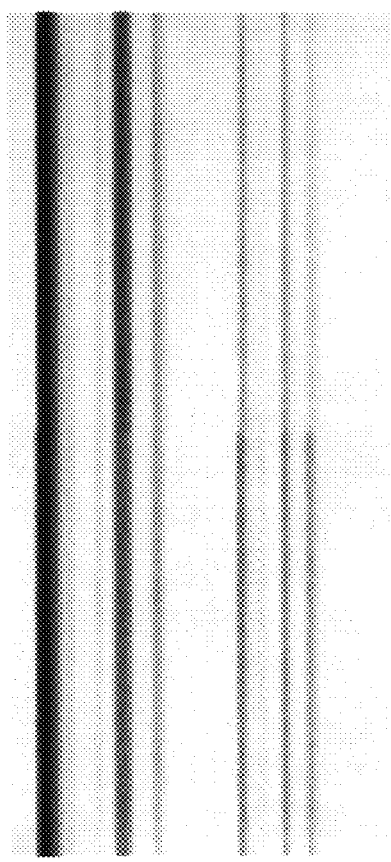
FIG. 4 is a depiction of the RiboPrint® patterns of helper bacterial strains. RiboPrint® patterns were obtained from B. cereus strain NRRL B-30268 (ADM 1A9) and NRRL B-30267 (ADM C12B).

Strains ADM C12B and ADM 1A9 were deposited at the Agricultural Research Service Culture Collection (NRRL), 1815 North University Street, Peoria, Ill. 61604, U.S.A., on Feb. 25, 2000 under the provisions of the Budapest Treaty and assigned accession numbers NRRL B-30267 and NRRL B-30268, respectively. RiboPrint® patterns obtained for strain NRRL B-30267 (ADM C12B) and strain NRRL B-30268 (ADM 1A9) are depicted in FIG. 4.

The helper strain is preferably incubated in an appropriate medium under suitable conditions for a sufficient amount of time until a culture of sufficient population is obtained. This helper strain inoculum can then be introduced into the culture medium for production of 2-KLG either separately or in combination with the inventive microorganism strains, i. e., a mixed inoculum. Preferably, the ratio of the amount of the helper strain relative to the amount of strain NRRL B-30265 (ADM 178–49) is in the range of from about 10:1 to about 1:10,000.

A further embodiment of the present invention provides a mixed microorganism culture which can be used in the inventive process. A preferred mixed microorganism culture according to the instant invention comprises a mixture formed from a biologically pure culture of a microorganism strain having the identifying characteristics of strain NRRL B-30266 and a biologically pure culture of a microorganism strain having the identifying characteristics of strain NRRL B-30265. The mixed microorganism culture of the present invention is characterized by the ability to produce 2-KLG from D-sorbitol in a yield of at least about 40 g/L, preferably at least 60 g/L, more preferably at least 80 g/L. The mixed culture can further comprise an additional microorganism strain which is capable of providing helper function.

The present invention also relates to the strains of the present invention transformed with vectors which optionally include at least one marker gene.

Recombinant constructs can be introduced into the bacterial strains of the present invention using well known techniques such as transduction, transfection, conjugation, and electroporation or other transformation methods. The vector can be, for example, a phage, plasmid, cosmid or a minichromosome.

As defined herein, "host" and "host cells" are synonymous with the cells of the microorganism strains of the present invention.

Polynucleotides of interest can be joined to a vector containing a selectable marker for propagation in the host. A plasmid vector can be introduced in a precipitate, such as a calcium phosphate precipitate, or in a complex with a charged lipid.

Preferred are vectors comprising cis-acting control regions to a polynucleotide of interest. Appropriate trans-acting factors can be supplied by the host, supplied by a complementing vector, or supplied by the vector itself upon introduction into the host.

In certain preferred embodiments in this regard, the vectors provide for specific expression, which can be inducible, mutant-specific and/or condition-specific. Particularly preferred among such vectors are those inducible by environmental factors that are easy to manipulate, such as temperature, nutrient additives or chemical additives. Other suitable environmental factors will be readily apparent to the skilled artisan.

Expression vectors useful in the present invention include chromosomal-, episomal-vectors, e.g., vectors derived from plasmids, bacteriophage, and vectors derived from combinations thereof, such as cosmids and phagemids.

A DNA insert of interest should be operatively linked to an appropriate promoter which is preferably a host-derived promoter. The expression constructs will further contain sites for transcription initiation, termination and, in the transcribed region, a ribosome binding site for translation. The coding portion of the mature transcripts expressed by the constructs will include a translation initiating codon appropriate for the host at the beginning and a termination codon appropriately positioned at the end of the polypeptide to be translated.

As indicated, the expression vectors will preferably include at least one marker capable of being selected or screened for. Such markers include amikacin, augmentin (amoxicillin plusclavulonic acid), ampicillin, cefazolin, cefoxitin, ceftazidime, ceftiofur, cephalothin, chloramphenicol, enrofloxacin, erythiromycin, florfenicol, gentamicin, imipenem, kanamycin, penicillin, sarafloxicin, spectinomycin, streptomycin, tetracycline, ticarcillin, or tilmicosin resistance genes. Preferred markers include ampicillin, chloramphenicol, erythromycin, kanamycin, penicillin, spectinomycin, streptomycin, and/or tetracycline. Other suitable markers will be readily apparent to the skilled artisan.

A preferred vector is pMF 1014-α (M. T. Follettie, "DNA Technology for *Corynebacterium glutamicum:* Isolation and Characterization of Amino Acid Biosynthetic Genes," Ph.D. Dissertation, Massachusetts Institute of Technology, Cambridge, Mass. (1989)), which comprises the pSR1-α replicon and a kanamycin resistance determinant. Specifically, pMF1014-α comprises the pSR1 replicon (Archer, J. A. et al., *J Gen. Microbiol.* 139:1753–1759 (1993)), and the pSR1-α mutation permitting replicative maintenance of the plasmid in *E. coli* hosts (Follettie Dissertation, 1989), and the Tn903-derived kanamycin resistance gene from plasmid pUC4K (Taylor, L. A. et al., *Nucleic Acids Res.* 16:358 (1988)).

Introduction of the construct into the host cell can be effected by calcium phosphate transfection, DEAE-dextran mediated transfection, cationic lipid-mediated transfection, electroporation and other transformation methods, transduction, infection or other methods. Such methods are described in many standard laboratory manuals, such as Davis et al., "Basic Methods in Molecular Biology," (1986).

Methods used and described herein are well known in the art and are more particularly described, for example, in J. H. Miller, *Experiments in Molecular Genetics,* Cold Spring Harbor Laboratory Press, Cold Spring Harbor, N.Y. (1972); J. H. Miller, *A Short Course in Bacterial Genetics,* Cold Spring Harbor Laboratory Press, Cold Spring Harbor, N.Y. (1992); M. Singer and P. Berg, *Genes & Genomes,* University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla. (1995); *Methods in Plant Molecular Biology and Biotechnology,* B. R. Glick and J. E. Thompson, eds., CRC Press, Boca Raton, Fla. (1993); P. F. Smith-Keary, *Molecular Genetics of Escherichia coli,* The Guilford Press, New York, N.Y. (1989); *Plasmids: A Practical Approach,* 2nd Edition, Hardy, K. D., ed., Oxford University Press, New York, N.Y. (1993); *Vectors: Essential Data,* Gacesa, P., and Ramji, D. P., eds., John Wiley & Sons Pub., New York , N.Y. (1994); *Guide to Electroporation and electrofusions,* Chang, D., et al., eds., Academic Press, San Diego, Calif. (1992); *Promiscuous Plasmids of Gram-Negative Bacteria,* Thomas, C. M., ed., Academic Press, London (1989); *The Biology of Plasmids,* Summers, D. K., Blackwell Science, Cambridge, Mass. (1996); *Understanding DNA and Gene Cloning: A Guide for the Curious,* Drlica, K., ed., John Wiley and Sons Pub., New York, N.Y. (1997); *Vectors: A Survey of Molecular Cloning Vectors and Their Uses,* Rodriguez, R. L., et al., eds., Butterworth, Boston, Mass. (1988); *Bacterial Conjugation,* Clewell, D. B., ed., Plenum Press, New York, N.Y. (1993); Del Solar, G., et al., "Replication and control of circular bacterial plasmids," *Microbiol. Mol. Biol. Rev.* 62:434–464(1998); Meijer, W. J., et al.,"Rolling-circle plasmids from *Bacillus subtilis:* complete nucleotide sequences and analyses of genes of pTA1015, pTA1040, pTA1050 and pTA1060, and comparisons with related plasmids from gram-positive bacteria," *FEMS Microbiol. Rev.* 21:337–368 (1998); Khan, S. A., "Rolling-circle replication of bacterial plasmids," *Microbiol. Mol. Biol. Rev.* 61:442–455 (1997); Baker, R. L., "Protein expression using ubiquitin fusion and cleavage," *Curr. Opin. Biotechnol.* 7:541–546 (1996); Makrides, S. C., "Strategies for achieving high-level expression of genes in *Escherichia coli,"* *Microbiol Rev.* 60:512–538 (1996);Alonso, J. C., et al., "Site-specific recombination in gram-positive theta-replicating plasmids," *FEMS Microbiol. Lett.* 142:1–10 (1996); Miroux, B., et al., "Over-production of protein in *Escherichia coli:* mutant hosts that allow synthesis of some membrane protein and globular protein at high levels," *J. Mol. Biol.* 260:289–298 (1996); Kurland, C. G., and Dong, H., "Bacterial growth inhibited by overproduction of protein," *Mol. Microbiol.* 21:1–4 (1996); Saki, H., and Komano, T., "DNA replication of IncQ broad-host-range plasmids in gram-negative bacteria," *Biosci. Biotechnol. Biochem.* 60:377–382 (1996); Deb, J. K., and Nath, N., "Plasmids of corynebacteria," *FEMS Microbiol. Lett.* 175:11–20 (1999); Smith, G. P., "Filamentous phages as cloning vectors," *Biotechnol.* 10:61–83 (1988); Espinosa, M., et al., "Plasmid rolling circle replication and its control," *FEMS Microbiol. Lett.* 130:111–120 (1995); Lanka, E., and Wilkins, B. M., "DNA processing reaction in bacterial conjugation," *Ann. Rev. Biochem.* 64:141–169 (1995); Dreiseikelmann, B., "Translocation of DNA across bacterial membranes," *Microbiol. Rev.* 58:293–316 (1994); Nordstrom, K., and Wagner, E. G., "Kinetic aspects of control of plasmid replication by anti-sense RNA," *Trends Biochem. Sci.* 19:294–300 (1994); Frost, L. S., et al., "Analysis of the sequence gene products of the transfer region of the F sex factor," *Microbiol. Rev.* 58:162–210 (1994); Drury, L., "Transformation ofbacteria by electroporation," *Methods Mol. Biol.* 58:249–256 (1996); Dower, W. J., "Electroporation of bacteria: a general approach to genetic transformation," *Genet. Eng.* 12:275–295 (1990); Na, S., et al., "The factors affecting transformation efficiency of coryneform bacteria by electroporation," *Chin. J. Biotechnol.* 11:193–198 (1995); Pansegrau, W., "Covalent association of the traI gene product of plasmid RP4 with the 5'-terminal nucleotide at the relaxation nick site," J. Biol. Chem. 265:10637–10644 (1990); and Bailey, J. E., "Host-vector interactions in *Escherichia coli,*" *Adv. Biochem. Eng. Biotechnol.* 48:29–52 (1993).

The following examples are illustrative only and are not intended to limit the scope of the invention as defined by the appended claims. It will be apparent to those skilled in the art that various modifications and variations can be made in the processes of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLE 1

Mutagenesis and Isolation of L-sorbose Producing Mutants from *Gluconobacter oxydans* ATCC 621 for the Single Stage Fermentation of 2-KLG Mutants of improved L-sorbose production for the single stage fermentation have been developed from *G. oxydans* ATCC 621 in this invention. Bacterial cultures were grown to log phase in PYM medium (D-mannitol 50 g/L, glycerol 5 g/L, peptone 10 g/L, yeast extract 10 g/L, pH 7.0), then pelleted by centrifugation and resuspended in 2 mL of TM buffer (Tris. HCl 6.0 g/L, maleic acid 5.8 g/L, $(NH_4)_2SO_4$ 1.0 g/L, $Ca(NO_3)_2$ 5.0 mg/L, $MgSO4.7H_2O$ 0.1 g/L, $FeSO_4.7H_2O$ 0.25 mg/L, adjusted to pH 6.0 using KOH, autoclaved 15 min. at 121° C.) in a sterile tube. The 2 ml cell suspension was mixed with 0.04 mL of 5.0 mg/mL solution of N'-nitro-nitrosoguanidine (NTG), then incubated at 30° C. for 30 min. An untreated cell suspension was similarly incubated as a control for estimating kill percentage.

After incubation, 10 mL of TM buffer was added to each tube, then the cells were pelleted by centrifugation, washed twice in TM buffer, then resuspended in 4.0 mL of 0.1 M $NaH_2PO_4$ buffer (pH 7.2 adjusted with KOH). The washed cell suspensions were further diluted in phosphate buffer, and aliquots were spread on plates of PYM medium, TBC medium (Difco Trypton 5 g/L, Yeast extract 3 g/L, $K_2HPO_4$ 7 g/L, $KH_2PO_4$ 3 g/L, $MgSO_4$ 0.1 g/L, NaCl 5 g/L, D-sorbitol 10 g/L, tetrazolium blue chloride 0.03 g/L, agar 15 g/L, pH 6.8) or FM10 agar medium (corn steep liquor 2% [dry solid], ADM soy soluble 0.6% [dry solid], L-sorbose 150–200 g/L, $CaCO_3$ 50 g/L, agar 15 g/L, pH 7.2). These plates were incubated at 30° C. for 2–3 days. Colonies were then counted or isolated from these plates. Relative to unmutagenized control cells, the kill percentage from NTG treatment was 60–80%. Strain ADM 205-95 (NRRL B-30266), a mutant derived from ATCC 621 (see FIG. 2 RiboPrint® patterns), was isolated from FM10 agar medium.

Subsequent tests of this strain were carried out in the shaker flask fermentation. One loopful culture of ADM 205-95 was inoculated into 250ml baffled shaker flask containing SM7 seed medium (Quest N-Z Soy™ 10 g/L, D-sorbitol 10 g/L., D-mannitol 20 g/L, corn steep liquor 2% dry solid, niacinamide 0.05 g/L, thiamine 0.3 g/L, pantothenic acid 0.4 g/L,p-aminobenzoic acid 0.2 g/L, pH 6.7), and incubated at 30° C. and 240 rpm shaker for 22 hours. Two mL of seed contents were used to inoculate 25 mL of fermentation medium FM11 (as described in FM10 medium except L-sorbose was replaced with 150–170 g/L D-sorbitol) in a 250 mL baffled shaker flask, and flasks were shaken for 24 hours at 30° C. and 240 rpm. The production of L-sorbose was assayed by high performance liquid chromatography (HPLC). Strain ADM 205-95 produced 145.8 and 153.7 g/L of L-sorbose with 91.6 and 93.4% of yield from D-sorbitol in these tests.

EXAMPLE 2

Mutagenesis and Isolation of 2-KLG Producing Mutants from *Ketogulonogenium robustum* ADM-X6L (NRRL B-21627) for the Single Stage Fermentation of 2-KLG Mutants selected for the production of 2-KLG in this invention have been developed from mutants derived from *K. robustum* ADM-X6L (NRRL B-21627, U.S. Pat. No. 5,834,231). Strain ADM 171-109, a mutant developed originally from ADM -X6L, has been improved for the production of 2-KLG, and showed a mild resistance to L-sorbose. This strain thereof was subjected to mutagenesis, and variants showing improvements on both 2-KLG production and L-sorbose resistance were recovered.

Bacterial cultures were grown in PYM medium to mid-log phase, then pelleted by centrifugation and resuspended in 2 mL of TM buffer in a sterile tube. The 2 mL cell suspension was mixed with 60 µL of a 5.0 mg/mL solution of NTG, then incubated at 30° C. for 30 minutes. After incubation, 10 mL of TM buffer was added to each tube, then the cells were pelleted by centrifugation, washed twice in TM buffer, then resuspended in 4.0 mL of 0.1 M $NaH_2PO_4$ buffer. The cell suspension was further diluted in phosphate buffer, and aliquots were spread on plates of CM6 agar medium or CM6 medium containing 16–18% L-sorbose (CM6 medium contained Difco Bacto Soytone™ 10 g/L, D-sorbitol 5 g/L, D-mannitol 10 g/L, malt extract 5 g/L, yeast extract 5 g/L, $K_2HPO_4$ 1 g/L, $KH_2PO_4$ 9 g/L, NaCl 5 g/L, pH adjusted to 7.2 prior to autoclaving, L-sorbose 160–180 g/L added separately after autoclaving). Plates were then incubated at 30° C. for 3 to 5 days. Colonies were counted from CM6 plates.

Relative to control cells without NTG treatment, the killing percentage of NTG mutagenized cells was 32%. Colonies growing on CM6–18% L-sorbose plates were picked randomly and then screened for improved 2-KLG production from L-sorbose. Strain ADM 178-49 (NRRL B-30265), which has been developed from mutants originally derived from ADM-X6L through several steps of mutagenesis and screening (see FIG. 3 RiboPrint® patterns), was isolated from the CM6 agar plate containing 18% L-sorbose. Subsequent tests of this strain were carried out in the shaker flask fermentation.

One loopful culture of ADM 178-49 (NRRL B-30265) was inoculated into 250 mL baffled shaker flask containing SM7 seed medium, and incubated at 30° C. and 240 rpm shaker for 22 hours. Two mL of seed contents were used to inoculate a baffled shaker flask containing 25 mL of fermentation medium FM10 and about 130 g/L of L-sorbose, and flasks were shaken for 72 hours at 30° C. and 240 rpm. Strain ADM 178-49 produced 62.6–67.8 g/L of 2-KLG with about 100% of yield from L-sorbose in these tests.

EXAMPLE 3

Mutagenesis and Isolation of Non-spore Forming Mutants from *Bacillus cereus* ADM C12B for the Nutrient Provider in the Single Stage Fermentation of 2-KLG ADM C 12B (NRRL B-30267) is a spore forming bacteria which has been isolated from an ADM research site and identified to be *Bacillus cereus*. This strain has been found to have the helper function for 2-KLG production in this invention. To further improve the fermentation process and to prevent cross contamination, non-spore forming mutants, which are preferred for this invention, have since been developed from this strain.

Strain *B. cereus* ADM C12B was grown in CM6 medium to mid-log phase, then pelleted by centrifugation and resuspended in 2 mL of TM buffer in a sterile tube. The 2 mL cell suspension was mixed with NTG at the final concentration of 50 $\mu$g/mL, then incubated at 30° C. for 30 minutes. After incubation, 10 mL of TM buffer was added to the tube. The cells were pelleted by centrifugation, washed twice in TM buffer, then resuspended in 4.0 mL of 0.1 M $NaH_2PO_4$ buffer. The cell suspension was further diluted in phosphate buffer, and aliquots were spread on plates of PYM agar medium. Plates were incubated at 30° C. for 3–5 days.

Colonies were then picked up and transferred to microplates containing PYM agar medium. Each well of microplate would contain only one isolate. After being incubated at 30° C. overnight, colonies were replica transferred to another microplate containing 200 $\mu$L per well of PYM liquid medium. Microplates containing liquid cultures were incubated at 32° C., 240 rpm in a water bath shaker for two days, then moved to 73–75° C. incubator for 30–35 minutes to heat kill the vegetative cells. Only spores would survive from this heat treatment.

Five $\mu$L of heat treated culture were transferred to another microplate containing fresh PYM liquid medium. These new microplates inoculated with heat treated cultures were then incubated again in the water bath shaker at 32° C., 240 rpm overnight. The growth optical density (OD) of each well in microplates was measured at 660 nm with a microplate reader. Non-spore forming mutants could not survive from the heat treatment and showed low OD. One of these mutants ADM 1A9 (NRRL B-30268) (see FIG. 4 RiboPrint® patterns) was selected for further examination of its helper function as described in Example 7.

EXAMPLE 4

The Development of Single Stage Fermentation of 2-KLG in the Shaker Flask.

To select appropriate mutants for the single stage fermentation, mixed cultures of mutants derived from both L-sorbose producing strains and 2-KLG producing strains were tested in the shaker flask. For example, mutants derived from *G. oxydans* ATCC 621, the L-sorbose producer, were tested in the D-sorbitol medium with the mixed culture of *K. robustum* ADM 178-49 (NRRL B-30265), the 2-KLG producer. For each tested mutant (culture 1 in Table 1), one loopful culture was inoculated into a 250 mL baffled flask containing 20 mL seed medium SM7. Then 100 $\mu$L of ADM 178-49 culture (culture 2) was inoculated into the same flask. After incubated at 30° C., 240 rpm shaker for 22 hours, two mL of seeds contents were used to inoculate 25 mL fermentation medium FM11 in a 250 mL baffled flask containing 100–150 g/L D-sorbitol. After shaken at 30° C., 240 rpm for 48 hours, the 2-KLG, L-sorbose, and D-sorbitol were assayed by HPLC (Table 1).

TABLE 1

| Mixed culture Culture 1/Culture 2 | D-sorbitol g/L | L-sorbose g/L | 2-KLG g/L | Yield % |
|---|---|---|---|---|
| 189-127/178-49 | 0.4 | 5.8 | 120.4 | 80.2 |
| 189-134/178-49 | 1.2 | 30.9 | 80.8 | 54.1 |
| 189-199/178-49 | 0.3 | 7.3 | 140.6 | 93.6 |

EXAMPLE 5

The Study of Single Stage Fermentation of 2-KLG Employing the Mixed Culture of an L-sorbose Producing Strain and a 2-KLG Producing Mutant To optimize a mixed culture for the single stage fermentation, besides the development of candidate mutants from both L-sorbose producing strain *G. oxydans* ATCC 621, and 2-KLG producing strain *K. robustum* NRRL B-21627, seed cultivation and ratio of mixed culture were also studied in this invention.

Strain ADM 178-49 (NRRL B-30265) was cultured in a 500 mL baffled shaker flask containing 50 mL CM6 medium, and shaken at 30° C., 240 rpm for 20 hours. In the same time, Strain ATCC 621 was cultured separately in a 500 mL baffled shaker flask containing 50 mL PYM medium, and shaken at 30° C., 240 rpm for 20 hours. After 20 hours, culture ADM 178-49 had $OD_{660nm}$ at 1.1, and culture ATCC 621 at 3.9. Both cultures were mixed at different ratios (for example, at 3:1, 2:1, 1:1, 1:2, and 1:3) and then stored at −72° C. deep freezer.

Two hundred $\mu$L of frozen mixed cultures each from different ratios were inoculated into the inoculation flasks containing 50 mL seed medium SM6, and shaken at 30° C., 240 rpm for 20 hours. The seeds were then inoculated into 1.5 L fermentors containing 800 mL fermentation medium FM5 ( $MgSO_4.7H_2O$ 2 g/L, $CaCO_3$ 25 g/L, corn steep liquor 2% dry solid, ADM soy soluble 0.6% dry solid, D-sorbitol 160 g/L, and antifoam 2 drops per fermentor). The fermentation was conducted for 50 hours under the following conditions: 30° C., 800 rpm of agitation, 1.6 VVM of aeration, pH maintained at 6.8 using 17% $NH_4OH$. The results are shown in Table 2.

TABLE 2

| Mixed culture of (ADM 178-49:ATCC 621) | 3:1 | 2:1 | 1:1 | 1:2 | 1:3 |
|---|---|---|---|---|---|
| 2-KLG (g/L) | 111 | 114.7 | 114.5 | 100.2 | 91.7 |
| Yield %* | 86 | 91 | 90 | 79 | 72 |

*The yield % was calculated as: (g of 2-KLG produced/g of D-sorbitol in the medium) × 100%

EXAMPLE 6

The Study of Soluble Soy Isolates used for the Single Stage Fermentation of 2-KLG Employing the Mixed Culture of Three Different Organisms In order to produce 2-KLG efficiently in the large scale fermentation, the single stage fermentation has been modified in this invention to employ three organisms and soluble soy isolates. Besides the L-sorbose producing strain *G. oxydans* ADM 205-95 and the 2-KLG producing strain *K. robustum* ADM 178-49, a third strain *B. cereus* ADM C12B which provided the helper function was employed in this invention. Two different soluble soy isolates, ADM Soy Soluble and ADM RO Concentrate, were also employed in this invention to supplement nutrients for the mixed culture.

In this example as shown in FIG. 1, three organisms were cultivated separately through propagation/seed stage before they were inoculated to the main fermentation medium. Frozen cultures of all three strains in 1.5 mL vials were inoculated separately into 2 L baffled flasks containing 250 mL SM7A (D-sorbitol 10 g/L, D-mannitol 20 g/L, soy peptone 10 g/L, yeast extract 3 g/L, $KH_2PO_4$ 9.52 g/L, $K_2HPO_4$ 12.18 g/L, niacinamide 0.05 g/L, thiamine 0.3 g/L, D-pantothenic acid 0.4 g/L, p-aminobezoic acid 0.2 g/L, pH 6.7). After 16–24 hours incubation at 30° C., 240 rpm shaker, 50 mL shaker flask culture from each strain was inoculated to separate 5 L fermentors containing 3.3 L propagation/seed medium (ADM soy soluble or ADM RO Concentrate 6 g/L dry solid, D-sorbitol 10 g/L, corn steep liquor 30 g/L dry solid, Quest Hy-Yeast 102.3 g/L, antifoam 0.8 mL/L, pH 6.75). The set points of fermentor for cultivation of both propagation and seed stages were: 500 rpm of agitation, 1.8–2.0 VVM of aeration, 30° C. of temperature, and 1–3 psi of head pressure. The pH of seed and propagation for ADM 178-49 was controlled at 6.75. Both ADM 205-95 and ADM C12B did not require pH control.

After 16–24 hours, 17.5–25 mL propagation cultures (either ADM 205-95 or ADM 178-49) was inoculated one more step to seed fermentor and incubated for another 16–24 hours with the same conditions and medium as in the propagation stage. 225 mL seed culture of ADM 205-95 was then removed and inoculated to a 5 L main fermentor containing 3.05 L main fermentation medium (D-sorbitol 155 g/L, ADM soy soluble or RO Concentrate 6 g/L dry solid, corn steep liquor 20 g/L dry solid, antifoam 0.3 ml/L, pH 6.75). The fermentation was managed with run parameters of temperature at 30° C., aeration at 1.8–2.0 VVM, and agitation at 650 rpm. There was no pH control at this stage.

After 12–16 hours, all D-sorbitol had been converted to L-sorbose and pH was adjusted back to 6.75 and controlled at 6.75 with $Ca(OH)_2$ slurry. Then 225 mL seed culture of ADM 178-49 and 1.5 mL propagation culture of ADM C12B were inoculated to the main fermentor. After 38–45 hours, the fermentation was stopped and sample was withdrawn for HPLC analysis. The results are shown in Table 3.

TABLE 3

| Soy Isolates | Growth $OD_{660\,nm}$ | Titer 2-KLG (g/L) | Total 2-KLG (g) | Yield (%) |
| --- | --- | --- | --- | --- |
| ADM Soy Soluble | 20.8 | 104 | 423 | 88.5 |
| ADM RO Concentrate | 22.5 | 102 | 424 | 88.5 |

EXAMPLE 7

The Study of Single Stage Fermentation of 2-KLG using Mixed Culture of Mutants Derived from Three Different Species The study of mutants for 2-KLG production in the single stage fermentation has been accomplished by using the same conditions as described in Example 6. ADM 205-95, an L-sorbose producing mutant derived from G. oxydans ATCC 621, ADM 178-49, a 2-KLG producing mutant developed from K. robustum ADM-X6L (NRRL-B-21627), and the helper strains B. cereus ADM C12B and its non-spore forming mutant ADM 1A9 were used in this study.

Frozen cultures of ADM 205-95, ADM 178-49, ADM C12B, and ADM 1A9 in 1.5 mL vials were inoculated separately into 2 L baffled flasks containing 250 mL SM7A. After 16–24 hours incubation at 30° C., 240 rpm shaker, 50 mL shaker flask culture from each strain was inoculated separately into 5 L propagation fermentors containing 3.3 L propagation/seed medium (ADM soy soluble 6 g/L dry solid, D-sorbitol 10 g/L, corn steep liquor 30 g/L dry solid, Quest Hy-Yeast 102.3 g/L, antifoam 0.8 mL/L, pH 6.75). The set points of fermentor for cultivation of both propagation and seed stages were: 500 rpm of agitation, 1.8–2.0 VVM of aeration, 30° C. of temperature, and 1–3 psi of head pressure. The pH of seed and propagation for ADM 178-49 was controlled at 6.75. Other strains did not require pH control.

Under the same cultivation conditions, 17.5–25 mL propagation culture of ADM 205-95 was then inoculated further to a seed fermentor containing 3.3 L propagation/seed medium and incubated for 16–24 hours. With the same conditions and medium, the propagation culture of ADM 178-49 was inoculated separately to another seed fermentor accordingly. About 225 mL of 13 hours old seed culture of ADM 205-95 was then removed and inoculated to a 5 L main fermentor containing 3.05 L main fermentation medium (D-sorbitol 155 g/L, ADM RO Concentrate 6 g/L dry solid, corn steep liquor 20 g/L dry solid, antifoam 0.3 ml/L, pH 6.75). The fermentation was managed with run parameters of temperature at 30° C., aeration at 1.8–2.0 VVM, and agitation at 650 rpm. There was no pH control at this stage.

After 12–16 hours, all D-sorbitol had been converted to L-sorbose and pH was adjusted back to 6.75 and controlled at 6.75 with $Ca(OH)_2$ slurry. Then 225 mL of 15–20 hours old seed culture of ADM 178-49 and 1.5 mL of 12 hours old propagation culture of ADM C12B or ADM 1A9 were inoculated to this main fermentor. After 38–45 hours, the fermentation was stopped and samples were analyzed with HPLC. The results are shown in Table 4.

TABLE 4

| Mixed Culture* | 2-KLG titer (g/L) | Total 2-KLG (g) | Yield (%) |
| --- | --- | --- | --- |
| A | 108 | 445 | 93.2 |
| B | 112 | 454 | 95.3 |

*In two separate main fermentors, the first fermentor was inoculated with mixed culture A which contained ADM 205-95, ADM 178-49, and ADM C12B; the second fermentor was inoculated with mixed culture B which contained ADM 205-95, ADM 178-49, and ADM 1A9.

What is claimed is:

1. A biologically pure culture of a microorganism strain comprising all of the identifying characteristics of a strain selected from the group consisting of NRRL B-30265, NRRL B-30266, NRRL B-30267 and NRRL B-30268, or a mutant thereof derived from said strain.

2. The biologically pure culture according to claim 1 comprising microorganism strain NRRL B-30265 or a mutant thereof derived from said strain.

3. The biologically pure culture according to claim 1 comprising microorganism strain NRRL B-30266 or a mutant thereof derived from said strain.

4. The biologically pure culture according to claim 1 comprising microorganism strain NRRL B-30267 or a mutant thereof derived from said strain.

5. The biologically pure culture according to claim 1, wherein said mutant is strain NRRL B-30268.

6. A microorganism culture system comprising a mixture formed from a biologically pure culture of a microorganism strain having all of the identifying characteristics of strain NRRL B-30266 and a biologically pure culture of a microorganism strain having all of the identifying characteristics of strain NRRL B-30265, wherein said culture system is capable of producing at least about 40 g/L of 2-keto-L-gulonic acid from D-sorbitol.

7. A process for the production of 2-keto-L-gulonic acid which comprises:
(a) culturing a microorganism strain comprising all of the identifying characteristics of NRRL B-30265 or a mutant thereof in mixed culture with a microorganism strain capable of converting D-sorbitol to L-sorbose in a medium containing D-sorbitol, for a time sufficient for said D-sorbitol to be converted to 2-keto-L-gulonic acid; and
(b) recovering said 2-keto-L-gulonic acid,
wherein said mutant is capable of producing at least about 40 g/L of 2-keto-L-gulonic acid in mixed culture.

8. The process according to claim 7, wherein said microorganism strain capable of converting D-sorbitol to L-sorbose is a member of the genus Gluconobacter or Acetobacter.

9. The process according to claim 8, wherein said microorganism strain is *Gluconobacter oxydans* ATCC 621 or a mutant thereof derived from said strain.

10. The process according to claim 9, wherein said mutant is selected from media containing at least about 100 g/L of L-sorbose.

11. The process according to claim 9, wherein said mutant is strain NRRL B-30266.

12. The process according to claim 7, wherein said microorganism strain comprising the identifying characteristics of NRRL B-30265 corresponds to strain NRRL B-30265.

13. The process according to claim 7, wherein said microorganism strain comprising all of the identifying characteristics of NRRL B-30265 corresponds to strain NRRL B-30265, and wherein said microorganism strain capable of converting D-sorbitol to L-sorbose is strain NRRL B-30266.

14. The process according to claim 7, wherein said mixed culture is capable of producing at least about 40 g/L of 2-keto-L-gulonic acid from D-sorbitol.

15. The process according to claim 7, wherein said 2-keto-L-gulonic acid is recovered as a salt thereof from said medium.

16. The process according to claim 7, further comprising converting said 2-keto-L-gulonic acid to ascorbic acid or a salt thereof.

17. The process according to claim 7, wherein said culturing is performed at a pH of about 5.0 to about 9.0.

18. The process according to claim 7, wherein said culturing is performed at a temperature of about 5° C. to about 36° C.

19. The process according to claim 7, wherein said D-sorbitol is present in the medium at a concentration from about 20 grams to about 250 grams per liter of medium.

20. The process according to claim 7, wherein the inoculum ratio of said microorganism strain comprising all of the identifying characteristics of NRRL B-30265 to said L-sorbose-producing strain is from about 10:1 to about 1:10.

21. The process according to claim 7, where said mixed culture comprises at least one additional microorganism strain.

22. The process according to claim 21, wherein said additional microorganism strain is a member of a genus selected from the group consisting of Aureobacterium, Corynebacterium, Bacillus, Brevibacterium, Pseudomonas, Proteus, Enterobacter, Citrobacter, Erwinia, Xanthomonas and Flavobacterium.

23. The process according to claim 22, wherein said additional microorganism strain is *Bacillus cereus*.

24. The process according to claim 23, wherein said *Bacillus cereus* strain is strain NRRL B-30267 or a mutant thereof derived from said strain.

25. The process according to claim 24, wherein said mutant is selected to be incapable of producing spores.

26. The process according to claim 25, wherein said mutant is strain NRRL B-30268.

27. The process according to claim 7, wherein said medium further comprises soybean products.

28. The process according to claim 27, wherein said soybean products comprise soy flour, soy protein and its hydrolysate, soy peptone, soluble soy isolates, soy whey or soy molasses.

29. The process according to claim 27, wherein said soybean products are derived from the processing of soy beans.

30. The process according to claim 28, wherein said soybean products comprise soluble soy isolates or soy whey.

31. The culture of claim 1, wherein said strain comprises a vector.

32. The culture of claim 31, wherein said vector comprises a marker gene.

33. The culture of claim 32, wherein said marker gene comprises a nucleotide sequence operative to direct synthesis of a protein conferring antibiotic resistance in a host cell.

34. The culture of claim 33, wherein said antibiotic resistance comprises resistance to ampicillin, chloramphenicol, erythromycin, kanamycin, spectinomycin, streptomycin or tetracycline.

35. The culture of claim 31, wherein said vector comprises:
(a) an exogenous terminator of transcription;
(b) an exogenous promoter; and
(c) a discrete series of restriction endonuclease recognition sites, said series being between said promoter and said terminator.

36. A method for transforming the strain according to claim 1, comprising inserting a vector into said strain.

* * * * *